United States Patent
Zhou et al.

(10) Patent No.: US 10,799,549 B2
(45) Date of Patent: Oct. 13, 2020

(54) HEPATOPROTECTIVE TRADITIONAL CHINESE MEDICINE COMPOSITION CONTAINING FRUCTUS LIGUSTRI LUCIDI, HERBA EXLIPTAE, RADIX PAEONIAE ALBA, RHIZOMA CURCUMAE LONGAE AND CLAM EXTRACT, PREPARATION METHOD AND USE THEREOF

(71) Applicant: INFINITUS (CHINA) COMPANY LTD., Jiang Men (CN)

(72) Inventors: Yong Zhou, Jiang Men (CN); Hailong Li, Jiang Men (CN); Xiaolei Guo, Jiang Men (CN); Chung Wah Ma, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 0 days.

(21) Appl. No.: 16/412,638

(22) Filed: May 15, 2019

(65) Prior Publication Data
US 2019/0269746 A1 Sep. 5, 2019

Related U.S. Application Data

(62) Division of application No. 15/223,131, filed on Jul. 29, 2016, now abandoned.

(30) Foreign Application Priority Data

Sep. 11, 2015 (CN) .......................... 2015 1 0577856

(51) Int. Cl.
| | | |
|---|---|---|
| *A61K 35/618* | (2015.01) | |
| *A61K 36/638* | (2006.01) | |
| *A61K 36/9066* | (2006.01) | |
| *A61K 36/28* | (2006.01) | |
| *A61K 36/65* | (2006.01) | |

(52) U.S. Cl.
CPC .......... *A61K 36/638* (2013.01); *A61K 35/618* (2013.01); *A61K 36/28* (2013.01); *A61K 36/65* (2013.01); *A61K 36/9066* (2013.01); *A61K 2236/33* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| 2006/0165636 A1* | 7/2006 | Hasebe | .................... A61K 8/88 |
| | | | 424/70.14 |
| 2015/0190450 A1* | 7/2015 | Chang | .................... A23L 33/10 |
| | | | 424/443 |

FOREIGN PATENT DOCUMENTS

| CN | 1943724 | * | 4/2007 |
| CN | 102512600 | | 6/2012 |
| CN | 103749825 | * | 4/2014 |
| CN | 104398986 | | 3/2015 |
| CN | 104474459 | | 4/2015 |
| CN | 104740541 | | 7/2015 |
| JP | 2004194616 | | 7/2015 |
| WO | WO 2017/124826 | | 7/2017 |

OTHER PUBLICATIONS

Chin-Lin H. et al. Hepatoprotection by Freshwater Clam Extract Against CCl4 Induced Hepatic Damage in Rats. J of Chinese Medicine 38(5)881-894, 2010. (Year: 2010).*

Database Biosis [Online] Biosciences Information Service, Philadelphia, PA, US; 2010, Hsu Chin-Lin et al., "Hepatoprotection by Freshwater Clam Extract Against CCl4-Induced Hepatic Damage in Rats," Database Accession No. PREV201000551886; & American Journal of Chinese Medicine, vol. 38, No. 5, 2010, pp. 881-894, ISSN: 0192-415X, DOI: 10.1142/S0192415X10008329.

Database Biosis [Online] Biosciences Information Service, Philadelphia, PA, US; 2010, Chi H. M. et al., "Protective Effects of Water Extract of Clam on Normal and CCl4-Induced Damage in Primary Cultured Rat Hepatocytes," Database Accession No. PREV201000643857; & American Journal of Chinese Medicine, vol. 38,No. 6, 2010,pp. 1193-1205, ISSN: 0192-415X, DOI: 10.1142/S0192415X10008561.

Database WPI, Week 201440, Thomson Scientific, London, GB; AN 2014-L88667, & CN103749825 A (Qingdao Hengbo Instr Co Ltd), Apr. 30, 2014.

Database WPI, Week 201535, Thomson Scientific, London, GB; AN 2015-269196 & CN104398986A (Qingdao Shenda High-Tech Dev Co Ltd), Mar. 11, 2015.

Extended European Search Report issued in European Patent Application No. 16184960.9, dated Feb. 3, 2017.

Office Communication issued in U.S. Appl. No. 15/223,131, dated Feb. 26, 2019.

Office Communication issued in U.S. Appl. No. 15/223,131, dated Oct. 19, 2018.

Office Communication issued in U.S. Appl. No. 15/223,131, dated Aug. 24, 2018.

(Continued)

*Primary Examiner* — Ralph J Gitomer
(74) *Attorney, Agent, or Firm* — Parker Highlander PLLC (57) ABSTRACT

Disclosed is a method of preparing a hepatoprotective traditional Chinese medicine composition. The composition is prepared from Fructus Ligustri Lucidi, Herba Ecliptae, Radix Paeoniae Alba, Rhizoma Curcumae Longae and clam as main raw materials.

7 Claims, 3 Drawing Sheets

(56) References Cited

OTHER PUBLICATIONS

Tang et al., "Protective effects of a traditional Chinese herbal formula Jiang-Xian HuGan on Concanavalin A-induced mouse hepatitis via NF-κB and Nrf2 signaling pathways," *Journal of Ethnopharmacology*, 217:118-125, 2018.

Office Communication issued in Chinese Patent Application No. 201510577856.X, dated Mar. 20, 2020. (English translation of Chinese text).

* cited by examiner

HEPATOPROTECTIVE TRADITIONAL CHINESE MEDICINE COMPOSITION CONTAINING FRUCTUS LIGUSTRI LUCIDI, HERBA EXLIPTAE, RADIX PAEONIAE ALBA, RHIZOMA CURCUMAE LONGAE AND CLAM EXTRACT, PREPARATION METHOD AND USE THEREOF

CROSS REFERENCE OF RELATED APPLICATION

The present application is a division of U.S. patent application Ser. No. 15/223,131, filed on Jul. 29, 2016, which application claims the priority of Chinese Patent Application No. 201510577856.X, filed with the Chinese Patent Office on Sep. 11, 2015, titled "Hepatoprotective Traditional Chinese Medicine Composition, Preparation Method and Use thereof", which applications are hereby incorporated by reference to the maximum extent allowable by law.

FIELD

The present invention relates to the technical field of traditional Chinese medicine, in particular to a hepatoprotective traditional Chinese medicine composition and a preparation method and use thereof.

BACKGROUND

Liver is an organ with a main function of metabolism in the body and plays a role in deoxidation, glycogen storage, synthesis of secreted proteins and the like inside the body. In the meantime, liver also secretes bile in the digestive system. It is mentioned in "Inner Canon of Huangdi-Plain Questions" that, the liver is to a human what a general officer out of which strategies come is to an army. According to traditional Chinese medicine, the liver, one of the five viscera, is in control of the angry mood, corresponds to wood in the five elements ("Five Elements Doctrine", a major Chinese medical doctrine. The doctrine holds that the universe and nature are composed of five basic elements, i.e., metal, wood, water, fire and earth, so is the human body. Only when the five elements in body works in harmony as a whole can health be reached), its position in guts looks very much like spring in the four seasons, and it is closely related to the gallbladder in the six entrails. The liver is responsible for catharsis and is in control of the angry mood. It is also in control of storing blood and is vividly called "a sea of blood" of human body. It is closely linked to human spirits & emotions, digestion & absorption, running of blood & qi (a metaphysical concept in traditional Chinese medicine (TCR). Its amount in body is positively related to the health, according to TCR), fluid metabolism, sex and reproduction.

Among modern professionals pursuing career success, there are general phenomena of fast-paced life, high work pressure and frequent staying up late to work overtime and the like, which readily cause blood shortage in the liver, thus bringing people into a sub-health state such as "uncontrollable fatigue", "no relief no matter how long you have a rest". Meanwhile, the early-stage diseases or disorders concerning the liver, which are not taken seriously, will cause greater harm later, and may even develop into liver fibrosis, liver cirrhosis, liver cancer, etc. In China, about 58.18% of the population are in a sub-health state, wherein up to 130 million people suffer from liver injury, and nearly 500,000 people die of diseases associated with liver injury. With the growing concerns over health issues, people have realized that once a problem appears in the liver, various subsequent symptoms naturally appear in the body. Therefore, liver nourishment and protection has gradually become an important part of health care.

Currently, there have been various types of hepatoprotective products on the market. However, Chinese herbal medicines are highly recognized in the population and favored by the Chinese people due to their unique advantages in liver nourishment and protection. Chinese patent CN104740541A, for example, discloses a health-care Chinese medicine powder that protects the liver, detoxifies it and restores its function, which is prepared by water decoction and spray drying from 33 kinds of Chinese herbal medicines including Radix Paeoniae Alba, Fructus Schisandrae Chinensis, Fructus Ligustri Lucidi, Herba Ecliptae, Fructus Lycii, Fructus Mori, Radix Angelicae Sinensis, Fructus Mume, Fructus Citri Sarcodactylis, Fructus Hordei Germinatus, Flos Rosae Chinensis, Rhizoma Curcumae Longae and the like. Compared to western medicines, Chinese medicines have lower side effects, but the side effects will correspondingly increase with the increase of the Chinese medicine components. Meanwhile, the medication safety cannot be guaranteed as the Chinese medicine components increase. The Chinese medicine powder disclosed in the Patent CN104740541A comprises up to 33 kinds of Chinese herbal medicines, besides the potential problems about medication safety, its high cost, and complicated process limit large-scale production thereof

SUMMARY

In view of the above mentioned example, the object of the present invention is to provide a hepatoprotective traditional Chinese medicine composition, which achieves a significant hepatoprotective efficacy with fewer components, and to provide a process for preparing it and its use.

To achieve the above object, the present invention provides the following technical solutions:

A hepatoprotective Chinese medicine composition, which is prepared by Fructus Ligustri Lucidi, Herba Ecliptae, Radix Paeoniae Alba, Rhizoma Curcumae Longae and clam.

According to Chinese medicine theories, the present invention selects three Chinese medicines, Fructus Ligustri Lucidi, Herba Ecliptae and Radix Paeoniae Alba, in combination with the extracts of Rhizoma Curcumae Longae and clam to prepare a Chinese medicine composition having a significant hepatoprotective efficacy through unique procedures. The Chinese medicine composition pays attention to not only the efficacy, but also reasonable combination of raw materials in the composition, and thus an optimal formula is obtained.

Among the selected Chinese medicine components, Fructus Ligustri Lucidi is the dry ripe fruit of *Ligustrum lucidum* Ait. in the Oleaceae family. As recorded in "Chinese Pharmacopoeia", it is sweet, bitter and cool in nature. It has the efficacies of nourishing the liver and the kidney, brightening eyes and blackening the hair with a dosage of 6-12 g. Clinically it is used to treat yin-deficiency of the liver and the kidney, dizziness, tinnitus, weak waist and knees, premature graying of the beard and the hair, dim eyes, internal heat, diabetes and hectic fever.

Herba Ecliptae is the dry aboveground part of *Eclipta prostrata* L. in the Asteraceae family. As recorded in "Chinese Pharmacopoeia", it is sweet, sour and cold in nature. It has the efficacies of nourishing the liver and the kidney, cooling the blood and hemostasis with a dosage of 6-12 g. Clinically it is used to treat yin-deficiency of the liver and the kidney, loose teeth, premature graying of the beard and the hair, dizziness, tinnitus, and weak waist and knees.

Radix Paeoniae Alba is the dry root of *Paeonia lactiflora* Pall. in the Ranunculaceae family. As recorded in "Chinese Pharmacopoeia", it is bitter, sour and slightly cold in nature, and goes to the liver and the spleen channels. It has the efficacies of nourishing the blood, regulating menstruation, astringing yin, suppressing sweating, nourishing the liver, relieving pain and stabilizing yang in the liver. It is used to treat blood deficiency, sallow complexion, irregular menstruation, spontaneous sweating, night sweating, hypochondriac pain, abdominal pain, limb spasm, headache and dizziness with a dosage of 6-15 g.

Rhizoma Curcumae Longae is the dry rhizome of *Curcuma longa* L. in the Zingiberaceae family. It is pungent, bitter and warm in nature, and goes to the spleen and the liver channels. It has the efficacies of invigorating blood and qi circulation and relieving dysmenorrhea with a dosage of 3-10 g. It is used to treat sharp pain in the chest and the lateral thorax, chest stuffiness, heartache, dysmenorrhea, amenorrhea, pelvic mass, shoulder and arm pain caused by rheumatism and swelling and pain due to trauma.

Clam is an ancient liver-nourishing tonic. As recorded in "Compendium of Materia Medica", "Claim mainly serves to stimulate appetite, inhibit toxicity of mineral medicines, eliminate sudden fever, brighten the eyes, induce diuresis, relieve alcoholism and treat yellowing of the eyes".

Preferably, the composition of the present invention is prepared by extracting Fructus Ligustri Lucidi, Herba Ecliptae and Radix Paeoniae Alba with ethanol and then mixing with Rhizoma Curcumae Longae extract and clam extract. The Rhizoma Curcumae Longae extract is an alcohol extract and the clam extract is a water extract.

Preferably, the parts by weight of the respective components are:

4-30 parts of Fructus Ligustri Lucidi, 2-15 parts of Herba Ecliptae, 2-15 parts of Radix Paeoniae Alba, 2-20 parts of the Rhizoma Curcumae Longae extract, and 2-10 parts of the clam extract.

Further preferably, the parts by weight of the respective components are:

10-25 parts of Fructus Ligustri Lucidi, 5-15 parts of Herba Ecliptae, 3-12 parts of Radix Paeoniae Alba, 6-18 parts of the Rhizoma Curcumae Longae extract, and 4-8 parts of the clam extract.

More preferably, the parts by weight of the respective components are:

20 parts of Fructus Ligustri Lucidi, 15 parts of Herba Ecliptae, 8 parts of Radix Paeoniae Alba, 12 parts of the Rhizoma Curcumae Longae extract, and 8 parts of the clam extract.

Meantime, in the specific embodiments of the present invention, the parts by weight of the raw materials of the traditional Chinese medicine composition may also be selected as follows:

20 parts of Fructus Ligustri Lucidi, 15 parts of Herba Ecliptae, 10 parts of Radix Paeoniae Alba, 10 parts of the Rhizoma Curcumae Longae extract, and 6 parts of the clam extract.

30 parts of Fructus Ligustri Lucidi, 5 parts of Herba Ecliptae, 5 parts of Radix Paeoniae Alba, 20 parts of the Rhizoma Curcumae Longae extract, and 5 parts of the clam extract.

5 parts of Fructus Ligustri Lucidi, 15 parts of Herba Ecliptae, 15 parts of Radix Paeoniae Alba, 2 parts of the Rhizoma Curcumae Longae extract, and 10 parts of the clam extract.

10 parts of Fructus Ligustri Lucidi, 5 parts of Herba Ecliptae, 15 parts of Radix Paeoniae Alba, 5 parts of the Rhizoma Curcumae Longae extract, and 5 parts of clam extract.

10 parts of Fructus Ligustri Lucidi, 15 parts of Herba Ecliptae, 10 parts of Radix Paeoniae Alba, 5 parts of Rhizoma Curcumae Longae extract, and 10 parts of clam extract.

Preferably, the Rhizoma Curcumae Longae extract is obtained by the following process:

Grinding the Rhizoma Curcumae Longae, then extracting it with ethanol, concentrating the extract solution underreduced pressure into an extractum, adding ethanol to dissolve the extractum, filtering, concentrating the filtrate, and drying to obtain the Rhizoma Curcumae Longae extract.

More preferably, the Rhizoma Curcumae Longae extract is obtained by the following process:

Grinding the Rhizoma Curcumae Longae, then extracting it with ethanol twice, combining the two extract solutions, concentrating it under reduced pressure into an extractum, adding ethanol to dissolve it, filtering, concentrating the filtrate, and drying to obtain the Rhizoma Curcumae Longae extract.

Preferably, the clam extract is obtained by the following process:

Washing the fresh clam, then boiling it with water, concentrating and filtering to obtain an extract solution of the clam, sterilizing, and then drying to obtain the clam extract.

More preferably, the clam extract is obtained by the following process:

Washing the fresh clam, then boiling it with water, concentrating and filtering to obtain an extract solution of the clam, cooling it to room temperature, then mixing it well with a spraying agent, sterilizing, and then spray drying to obtain the clam extract. Wherein, the spraying agent is selected from excipients conducive to the smooth spraying such as maltodextrin, isomalto oligosaccharide powder, β-cyclodextrin, starch and the like.

In addition to the corresponding extracts obtained by the processes for extracting Rhizoma Curcumae Longae and clam defined in the present invention, commercially available corresponding extracts can also be directly used in the present invention. For example, the Rhizoma Curcumae Longae extract can be purchased from Ningbo Traditional Chinese Medicine Pharmaceutical Co. Ltd., and the clam extract can be purchased from Guangzhou Jingfang Pharmaceutical Technology Development Co. Ltd./Guangzhou Mandy Biotechnology Co. Ltd. (produced by Lichuan Farm Co. Ltd.).

In the hepatoprotective experiment of rat models of liver injury caused by carbon tetrachloride in combination with a hyperthermia Chinese medicine, compared to the model group, the Chinese medicine composition of the present invention can inhibit weight loss, significantly reduce ALT (alanine aminotransferase) and ALD (aldosterone), elevate ALB (albumin), increase SOD (superoxide dismutase), reduce MDA (malondialdehyde) and HYP (hydroxyproline), and meantime have a good effect in the evaluation of pathological changes. Based on the above technical effects, the present invention provides use of the Chinese medicine composition in the preparation of a hepatoprotective health product.

The health product may be of any dosage form in the current field of health product, and is preferably in the form of oral liquid, capsule, tablet, powder or granule. Each dosage form may be prepared by selecting suitable and acceptable excipients according to practical requirements of the dosage form, which belongs to conventional preparation techniques of dosage forms in the art.

The present invention also provides a method of preparing a hepatoprotective health product, comprising providing the traditional Chinese medicine composition as mentioned above.

In some embodiments, the hepatoprotective health product is in the form of oral liquid, capsule, tablet, powder or granule.

Additionally, the present invention also provides a method for preparing the Chinese medicine composition of the present invention, comprising:

step 1, extracting Fructus Ligustri Lucidi, Herba Ecliptae and Radix Paeoniae Alba with ethanol and concentrating the extract solution to obtain an alcohol extract of the three components;

step 2, mixing the alcohol extract of Fructus Ligustri Lucidi, Herba Ecliptae and Radix Paeoniae Alba with the Rhizoma Curcumae Longae extract and clam extract to obtain the Chinese medicine composition.

More preferably, the preparation method comprises:

step 1, extracting Fructus Ligustri Lucidi, Herba Ecliptae and Radix Paeoniae Alba with added ethanol, combining the extract solutions, filtrating, concentrating the filtrate in vacuum into an extractum, and spray-drying to obtain the alcohol extract of the mixed Fructus Ligustri Lucidi, Herba Ecliptae and Radix Paeoniae Alba;

step 2, mixing the alcohol extract of the mixed Fructus Ligustri Lucidi, Herba Ecliptae and Radix Paeoniae Alba with the Rhizoma Curcumae Longae extract and clam extract to obtain the Chinese medicine composition.

The present invention utilizes Fructus Ligustri Lucidi and Herba Ecliptae to nourish the liver blood, Radix Paeoniae Alba and Rhizoma Curcumae Longae to promote Qi flow of the liver, and clam to detoxify the liver. It combines several medicines to nourish the liver, smooth the liver qi and achieves a liver nourishing and protective efficacy, and is applicable to the population suffering from liver injury caused by an unhealthy lifestyle. The Chinese herbal medicine composition of the present invention is characterized in using Fructus Ligustri Lucidi, Herba Ecliptae, Radix Paeoniae Alba, Rhizoma Curcumae Longae and clam as main raw materials. It combines various components reasonably, uses them in conjunction, and achieves a health-care function via multiple means and at multiple levels.

DETAILED DESCRIPTION

The present invention discloses a hepatoprotective traditional Chinese medicine composition and a preparation method and use thereof. Those skilled in the art can carry it out with reference to the contents herein by making suitable improvements to process parameters. It should be particularly noted that all similar replacements and modifications are apparent to those skilled in the art, and are regarded to be within the present invention. The traditional Chinese medicine composition and the preparation method and use thereof in the present invention have been illustrated via preferred examples. Apparently, the method and use described herein can be modified or varied and combined properly by relevant personnel to implement and apply the inventive technique without departing from the contents, spirit and scope of the present invention.

The hepatoprotective traditional Chinese medicine composition and the preparation method and use thereof provided in the present invention are further illustrated as follows to demonstrate the present invention. It is necessary to point out that the following specific examples are only for further demonstrating the present invention, and should not be deemed as restricting the protection scope of the present invention. The non-substantial modification or adjustment made by others according to the present invention still falls into the protection scope of the present invention.

Example 1: The Traditional Chinese Medicine Composition of the Present Invention 1. Raw Materials 20 parts of Fructus Ligustri Lucidi, 15 parts of Herba Ecliptae, 10 parts of Radix Paeoniae Alba, 10 parts of Rhizoma Curcumae Longae extract, and 6 parts of clam extract.

2. Preparation Method

Ethanol was added to Fructus Ligustri Lucidi, Herba Ecliptae and Radix Paeoniae Alba for extraction. The extract solutions were combined and filtered. The filtrate was concentrated in vacuum into an extractum, which was subjected to spray drying to obtain an alcohol extract of the mixed Fructus Ligustri Lucidi, Herba Ecliptae and Radix Paeoniae Alba to be used.

The Rhizoma Curcumae Longae was ground, and then extracted with ethanol for two times. The extract solutions were combined and concentrated under reduced pressure into an extractum, to which ethanol was added for dissolution. The mixture was filtered. The filtrate was concentrated and dried to obtain a Rhizoma Curcumae Longae extract to be used.

After washing, the fresh clam was cooked with added water. An extract solution of the clam was obtained after concentration and filtration. The extract solution of the clam was cooled to room temperature, and then mixed well with added maltodextrin and isomalto oligosaccharide powder. The mixture was sterilized and then spray dried to obtain a clam extract to be used.

The alcohol extract of the mixed Fructus Ligustri Lucidi, Herba Ecliptae and Radix Paeoniae Alba was mixed with the Rhizoma Curcumae Longae extract and clam extract to obtain the traditional Chinese medicine composition.

Example 2: The Traditional Chinese Medicine Composition of the Present Invention 1. Raw Materials 30 parts of Fructus Ligustri Lucidi, 5 parts of Herba Ecliptae, 5 parts of Radix Paeoniae Alba, 20 parts of Rhizoma Curcumae Longae extract, and 5 parts of clam extract.

2. Preparation Method

The same as Example 1, wherein the Rhizoma Curcumae Longae extract and clam extract were commercially available products.

Example 3: The Traditional Chinese Medicine Composition of the Present Invention 1. Raw Materials 5 parts of Fructus Ligustri Lucidi, 15 parts of Herba Ecliptae, 15 parts of Radix Paeoniae Alba, 2 parts of Rhizoma Curcumae Longae extract, and 10 parts of clam extract.

2. Preparation Method

The same as Example 1.

Example 4: The Traditional Chinese Medicine Composition of the Present Invention 1. Raw Materials 20 parts of Fructus Ligustri Lucidi, 15 parts of Herba Ecliptae, 8 parts of Radix Paeoniae Alba, 12 parts of Rhizoma Curcumae Longae extract, and 8 parts of clam extract.

2. Preparation Method

The same as Example 1.

Example 5: The Traditional Chinese Medicine Composition of the Present Invention 1. Raw Materials 10 parts of Fructus Ligustri Lucidi, 5 parts of Herba Ecliptae, 15 parts of Radix Paeoniae Alba, 5 parts of Rhizoma Curcumae Longae extract, and 5 parts of clam extract.

2. Preparation Method

The same as Example 1.

Example 6: The Traditional Chinese Medicine Composition of the Present Invention 1. Raw Materials 10 parts of Fructus Ligustri Lucidi, 15 parts of Herba Ecliptae, 10 parts of Radix Paeoniae Alba, 5 parts of Rhizoma Curcumae Longae extract, and 10 parts of clam extract.

2. Preparation Method

The same as Example 1.

Example 7: An Experiment for Demonstrating Hepatoprotective Efficacy of the Traditional Chinese Medicine Composition of the Present Invention An experiment for demonstrating the efficacy using the traditional Chinese medicine composition provided in Example 4 above was carried out. Methods and results of the experiment were as follows.

1. Experimental Unit

Pharmacological and toxicological laboratory, School of Pharmacy, Zhongshan University.

2. Object of the Experiment

To study the hepatoprotective effect of the traditional Chinese medicine composition of the present invention on rat models of liver injury caused by carbon tetrachloride in combination with hyperthermia traditional Chinese medicines.

3. Experimental Animals

Wista rats, half male and half female, weight: females weigh (100-138 g, 118±14 g), males weigh (110-182 g, 150±18 g), provided by Experimental Animal Center, Zhongshan University. Usage license: SYXK (Yue) 2011-0112, production license: SCXK (Yue) 2011-0029.

4. Feeding Management of the Animals

Feeding room: animal room in sterile environment is on the second floor of the Experimental Animal Center (north campus), Zhongshan University. Experimental animal usage license No.: SYXK (Yue) 2007-0081.

Temperature: 20~25° C.; humidity: 40%-65%.

5. Feed

Type: Sterilized rat feed. Production unit: Guangdong Medical Laboratory Animal Center. Address: 119 Poyang Road, Huang Qi Town, Nanhai District, Foshan City. Production license: SCXK (Yue) 2008-0002.

Feeding method: free feed intake.

Routine nutrient index of the feed is detected twice a year by Experimental Animal Monitoring Department, Guangdong (with reference to the national standard of China GB14924.3-2010).

Feed storage: stored in a special feed room and kept ventilative, clean and dry.

6. Drinking Water:

Type of the drinking water: high quality water sterilized at 121° C. (1.0 kg/cm2) for 30 min, which meets "Water Quality Standards for Fine Drinking Water" (CJ94-2005).

Water feeding method: free intake through animal drinking bottles.

7. Main Equipments and Reagents 7.1 Main Equipments

Bio-Tek microplate reader (Bio-Tek company, U.S.), 5417R benchtop refrigerated high-speed centrifuge (EPPDORFF company, Germany), PL303101 electronic balance (Metter-Toled company), WFZ800-D3B UV-visible spectrophotometer (Ruili Analytical Instrument company, Beijing), BIOSPEC handheld tissue homogenizer (BIOSPEC company), BIO-RAD electrophoresis electroporator (BIO-RAD Company, U.S.), ImageQuant LAS 4000mini chemiluminescent imager (General Electric company, U.S.)

7.2 Main Reagents

Carbon tetrachloride (Tianjin Baishi Chemical Industry Co. Ltd., batch number 20130829), hydroxyproline (Hyp), superoxide dismutase (SOD), malondialdehyde (MDA), Coomassie brilliant blue protein kit (all purchased from Nanjing JianCheng Bioengineering Institute with batch numbers 20140711, 20140714, 20140710, 20140725, respectively), NOX2 antibody (Upstate, Millipore, USA), alanine aminotransferase (ALT), albumin (ALB), aldosterone (ALD) ELISA kit (all provided by Shanghai BlueGene Biotech Co. Ltd., batch number 20140813).

8. Experimental Design 8.1. Model Preparation

Wistar rats, half male and half female. The animal models were injected subcutaneously with a 40% peanut oil solution of $CCl_4$ twice a week at 3 ml/kg each time for 5 consecutive weeks. In the 6th week, they were injected once a week instead. In the 5th and 6th weeks, they were additionally intragastrically administrated with the above hyperthermia Chinese medicine at 15 ml/kg once a day for 2 weeks in total. The normal group was injected subcutaneously with the solvent, peanut oil twice a week at 3 ml/kg each time for 5 consecutive weeks. From the 6th week, they were injected once a week instead.

8.2 Grouping of the Animals

Grouping of the experiment: control group (solvent control), model group (a 40% peanut oil solution of $CCl_4$), treatment groups A and B (high dosage of the sample and low dosage of the sample), positive medicine group (yiguan decoction group), and treatment groups C, D and E.

8.3 Administration

Administration routes and the reason for the selection: intragastric administration through the mouth, which was the same as the clinical administration routes.

Administration frequency: once a day for 2 weeks in total.

8.4 Calculation of Administration Dosages 8.4.1 Conversion of Equivalent Dosages for Rats and for Human $$D(b)=D(a)*(Kb/Ka)*(Wa/Wb)^{1/3}$$

The body coefficient of human Ka: 0.1057, the body coefficient of rats Kb: 0.086, the standard weight of human Wa was calculated as 70 kilograms, the weight of rats Wb was calculated as a weight of about 0.25 kilogram at our current stage, the dosage for human was D(a), and the dosage for rats was D(b).

dosage for rats=dosage for human*(0.086/0.1057)*
(70/0.25)$^{1/3}$=5.3*dosage for human=5.3 times
the dosage for human 8.4.2 Hyperthermia Traditional Chinese Medicine 26 g/70 kg·d of the crude medicine for adults, namely 0.371 g/kg/day and 37.1 mg/100 g/day for human, which corresponds to 196 mg/100 g/day after conversion and is taken as 200 mg/100 g/day for rats.

Dried ginger, origin: Sichuan, batch number: 1401087; Aconitum carmichaeli, origin: Sichuan, batch number: D1311013; cinnamon: origin: Guangxi, batch number: 1401094. They were purchased from Sichuan New Lotus Chinese Herbal Medicine Co. Ltd.

The aconitum carmichaeli, cinnamon and dried ginger (1:1:1) were extracted with water. Specifically, the aconitum carmichaeli was firstly decocted for 1 h, then cinnamon and dried ginger were added to decoct together for 20 min. The decoction was concentrated to 1.2 g of crude medicines per milliliter. The obtained mixture was intragastrically administered once a day at an administration volume of 1.5 ml/100 g.

8.4.3 Yiguanjian Aconitum

As the positive medicine group, the dosage was 70 g/70 kg/day of the crude medicine, namely 100 mg/100 g/day for human, corresponding to 530 mg/100 g/day for rats.

Radix Angelicae Sinensis, origin: Gansu, batch number: 140101; *Adenophora stricta*, origin: Shandong, batch number: YPA4B0001; MeLia toosendan, batch number: YPA2K0001; *Ophiopogon japonicus*, origin: Hubei, batch number: 140401; *Lycium barbarum*, batch number: YPA4A0007; Dried rehamnnia root, batch number: YPA3J0001. They were purchased from Caizhilin Pharmacy, Guangzhou Pharmaceutical Group.

The compound formula of MeLia toosendan, Radix Angelicae Sinensis, *Adenophora stricta, Ophiopogon japonicus, Lycium barbarum* and Dried rehamnnia root (1:1.8:1.8:1.8:4:3.6) was extracted with water. Specifically, they were soaked with cold water for 30 min, and then decocted twice for 45 min and 30 min, respectively. The combined decoctions were concentrated until 0.9 g of the crude medicines per milliliter was achieved. It was administered with 0.75 ml/100 g, corresponding to an administration dosage of the crude medicine of 0.675 g/100 g, approximately 1 time the clinical administration dosage.

8.4.4 Treatment Group

A: the dry extract powder obtained by alcohol extraction of the medicinal materials of Fructus Ligustri Lucidi, Herba Ecliptae and Radix Paeoniae Alba and drying was formulated into tablets together with the clam extract and Rhizoma Curcumae Longae extract (the traditional Chinese medicine composition of Example 4) after addition of 35% dextrin. The recommended dosage for human is 3.6 g/day, which, after conversion, corresponds to an administration dosage for rats of 27.34 mg/100 g/day as the low dosage group. The dosage in the high dosage group A was 3 times as much as that in the low dosage: 81 mg/100 g/d.

B: the dry extract powder obtained by alcohol extraction of the medicinal materials of Fructus Ligustri Lucidi, Herba Ecliptae and Radix Paeoniae Alba and drying was formulated into tablets after addition of 35% dextrin. The recommended dosage for human is 0.6 g/day, which, after conversion, corresponds to an administration dosage for rats of 4.56 mg/100 g/day as the low dosage group B. The dosage in the high dosage group B was 3 times as much as that in the low dosage group B.

Group C: the dry extract powder obtained by alcohol extraction of Fructus Ligustri Lucidi and Herba Ecliptae and vacuum drying. The administration dosage for rats was set to 18.11 mg/100 g/day.

Group D: the dry extract powder obtained by vacuum drying of the alcohol extract of Radix Paeoniae Alba. The administration dosage for rats was set to 4.53 mg/100 g/day.

Group E: the clam extract and Rhizoma Curcumae Longae extract in Example 4 (8:5). The administration dosage for rats was set to 10.53 mg/100 g/day.

9. Experimental Method

At the end of the 8th week, the rats were intraperitoneally injected with 10% urethane to anesthetize them. Their abdominal cavities were dissected rapidly. Blood was taken from the abdominal veins with a sterile syringe and put in an ordinary blood tube. The blood was centrifuged at 3000r·min$^{-1}$ at a low temperature (2-8° C.) for 15 min. The plasma was stored at −20° C. till detection. The left lobe of the liver was fixed in 10% formalin. In addition, liver tissue was taken and stored in a refrigerator at −80° C. till the detection.

9.1 Observation of Symptoms and Signs of the Rats

The hair, activity, stool, water intake, weight and the like of the rats in the control group, model group and administration group were observed.

9.2 Detection of Serum Indexes

Alanine aminotransferase (ALT), albumin (ALB) and aldosterone (ALD) in the serum samples were determined with an ELISA kit according to the method in the instructions.

9.3 Detection of Liver Indexes

A liver tissue was taken, weighed, and then added with an appropriate amount of physiological saline. A 10% homogenate was prepared with a homogenizer in an ice bath. The total protein content in the homogenate of the liver tissue was determined by the Coomassie Brilliant Blue method. Malondialdehyde (MDA) was determined by TBA method and superoxide dismutase (SOD) by xanthine oxidase method according to instructions of the kit. In addition, after weighing of the liver tissue, hydroxyproline (HYP) was determined by alkaline hydrolysis of the sample according to instructions of the kit.

9.4 Pathological Examination of the Liver Tissue

The liver tissue was fixed with 10% formalin, dehydrated, paraffin embedded, sectioned and subjected to hematoxylin-eosin staining (HE) for the pathological morphology examination.

9.5 Statistical Processing

All data were expressed in the form of mean±standard deviation, analyzed with SPSS10.0 statistical software, and subjected to one-way analysis of variance and a pairwise comparative examination by the LSD method. $p<0.05$ represents statistical significance.

10. Experimental Results 10.1 Observations of the General State of the Rats

No death of the rats occurred in the solvent control group. They were well developed, active and lively with smooth and glossy coat. The animals in the model group were in a poor mental state and less active, with flabby coat and a weight loss (see Table 1).

TABLE 1

Effect on weights of rat models of liver injury caused by $CCl_4$ in combination with hyperthermia traditional Chinese medicine

| Group | Weight (g) 6th week | Weight (g) 8th week |
|---|---|---|
| Solvent control group (n = 9) | 315.4 ± 47.5 | 348.4 ± 47.1 |
| Model group (n = 8) | 289.6 ± 47.3 | 312.5 ± 46.7 |
| Low dosage group A (n = 8) | 279.0 ± 34.9 | 309.5 ± 47.6 |
| High dosage group A (n = 8) | 295.0 ± 57.9 | 325.1 ± 63.9 |
| Low dosage group B (n = 8) | 289.3 ± 41.5 | 321.3 ± 47.1 |
| High dosage group B (n = 8) | 296.5 ± 59.3 | 311.7 ± 61.6 |
| Positive control group (n = 8) | 297.6 ± 48.9 | 320.5 ± 52.8 |
| Group C (n = 7) | 283.1 ± 38.3 | 303.0 ± 48.3 |
| Group D (n = 7) | 286.4 ± 36.6 | 300.7 ± 49.6 |
| Group E (n = 7) | 295.8 ± 42.8 | 311.0 ± 42.7 |

P < 0.05 compared to the solvent control group,
P < 0.01 compared to the solvent control group;
*P < 0.05 compared to the model group,
**P < 0.01 compared to the model group.

All of the rats in the model group suffered from a weight loss. After treatment, the high dosage treatment group A and the positive control group had an inhibitory effect on the weight loss, but without significant difference.

10.2 Effect on Serum ALT, ALB and ALD of the Rats

Table 2 Effect on serum ALT, ALB and ALD of the rat models of liver injury caused by $CCl_4$ in combination with hyperthermia traditional Chinese medicine (R+s)

TABLE 2

Effect on serum ALT, ALB and ALD of the rat models of liver injury caused by $CCl_4$ in combination with hyperthermia traditional Chinese medicine ($\bar{X} \pm s$)

| Group | ALT/U · L$^1$ | ALB/g · L$^1$ | ALD/ng · L$^1$ |
|---|---|---|---|
| Solvent control group (n = 9) | 10.7 ± 13.3 | 13.9 ± 12.9 | 76.9 ± 19.0 |
| Model group (n = 8) | 131.4 ± 30.4## | 28.7 ± 9.3## | 121.2 ± 30.8## |
| Positive control group (n = 8) | 100.4 ± 24.3* | 35.4 ± 7.7 | 91.1 ± 23.8* |
| Low dosage group A (n = 8) | 103.9 ± 22.9* | 35.0 ± 12.8 | 98.5 ± 34.1 |
| High dosage group A (n = 8) | 85.3 ± 28.1** | 38.7 ± 7.5* | 91.5 ± 29.1* |
| Low dosage group B (n = 8) | 107.7 ± 21.2 | 31.6 ± 9.2 | 103.1 ± 33.2 |
| High dosage group B (n = 8) | 99.5 ± 27.1* | 31.2 ± 9.6 | 99.2 ± 28.8 |
| Treatment group C (n = 7) | 111.2 ± 25.9 | 32.9 ± 8.9 | 103.7 ± 26.7 |
| Treatment group D (n = 7) | 120.3 ± 29.1 | 26.8 ± 11.6 | 116.4 ± 24.8 |
| Treatment group E (n = 7) | 107.1 ± 28.8 | 31.2 ± 9.1 | 104.6 ± 32.5 |

P < 0.05 compared to the solvent control group,
P < 0.01 compared to the solvent control group;
*P < 0.05 compared to the model group,
**P < 0.01 compared to the model group.

Compared to the normal group, serum ALT in the model group was significantly increased. After treatment, the low and high dosage treatment groups A, the high dosage treatment group B and the positive control group had an inhibitory effect on the ALT increase with a significant difference.

Compared to the normal group, serum ALB in the model group significantly decreased. After treatment, the high dosage treatment group A had an inhibitory effect on the ALB decrease with a significant difference. The rest groups had an inhibitory effect on the ALB decrease.

Compared to the normal group, serum ALD in the model group significantly increased. After treatment, the high dosage treatment group A and the positive control group had an inhibitory effect on the ALD increase with a significant difference. The rest groups had an inhibitory effect on the ALD increase.

10.3 Effect on SOD and MDA in the Liver Homogenate and HYP in the Liver Tissue of Rats

TABLE 3

Effect on SOD and MDA in the liver tissue homogenate and HYP in the liver tissue of the rat models of liver injury caused by $CCl_4$ in combination with hyperthermia traditional Chinese medicine ($\bar{X} \pm s$)

| Group | SOD/U · mg$^1$ | MDA/ μmol · g$^1$ | HYP/μg · g$^1$ |
|---|---|---|---|
| Solvent control group (n = 9) | 111.2 ± 27.1 | 0.62 ± 0.11 | 119.2 ± 31.1 |
| Model group (n = 8) | 64.2 ± 21.3## | 1.37 ± 0.38## | 295.1 ± 50.6## |
| Positive control group (n = 8) | 93.4 ± 26.1* | 0.85 ± 0.25** | 222.1 ± 54.1** |
| Low dosage group A (n = 8) | 87.1 ± 23.9 | 1.05 ± 0.34* | 234.8 ± 36.9** |
| High dosage group A (n = 8) | 94.6 ± 29.9* | 0.91 ± 0.19* | 209.4 ± 51.7** |
| Low dosage group B (n = 8) | 84.5 ± 25.2 | 1.11 ± 0.29 | 228.9 ± 50.7** |
| High dosage group B (n = 8) | 92.0 ± 22.4* | 0.99 ± 0.27* | 211.6 ± 57.1** |
| Treatment group C (n = 7) | 85.1 ± 24.4 | 1.07 ± 0.27* | 248.5 ± 38.1 |

TABLE 3-continued

Effect on SOD and MDA in the liver tissue homogenate and HYP in the liver tissue of the rat models of liver injury caused by CCl$_4$ in combination with hyperthermia traditional Chinese medicine ($\overline{X} \pm s$)

| Group | SOD/U · mg$^1$ | MDA/ μmol · g$^1$ | HYP/ug · g$^1$ |
|---|---|---|---|
| Treatment group D (n = 7) | 77.2 ± 21.6 | 1.10 ± 0.29 | 257.6 ± 46.8 |
| Treatment group E (n = 7) | 76.6 ± 15.8 | 1.08 ± 0.30 | 248.8 ± 42.2 |

P < 0.05 compared to the solvent control group,
P < 0.01 compared to the solvent control group;
*P < 0.05 compared to the model group,
**P < 0.01 compared to the model group.

Compared to the normal group, SOD in the liver tissue in the model group decreased. After treatment, the high dosage treatment group A, the high dosage treatment group B and the positive control group had an inhibitory effect on the SOD decrease with a significant difference. The rest groups had an inhibitory effect on the SOD decrease.

Compared to the normal group, MDA in the liver tissue in the model group was increased. After treatment, the low and high dosage treatment groups A, the high dosage treatment group B, the treatment group C and the positive control group had an inhibitory effect on the MDA increase with a significant difference. The rest groups had an inhibitory effect on the MDA increase.

Compared to the normal group, HYP content in the liver tissue in the model group was increased. After treatment, the low and high dosage treatment groups A, the low and high dosage treatment groups B and the positive control group had an inhibitory effect on the increase of the HYP content with a significant difference. The rest groups had an inhibitory effect on the increase of the HYP content.

10.4 Pathological Effect on the Liver Tissue

TABLE 4

Grading standard of histopathologic changes

| Pathological injury range | Degree classification | Score |
|---|---|---|
| No histologic change observed | Normal | 0 |
| 0%-20% | Mild | 1 |
| 21%-40% | Moderate | 2 |
| 41%-100% | Severe | 3 |

Figure 1:
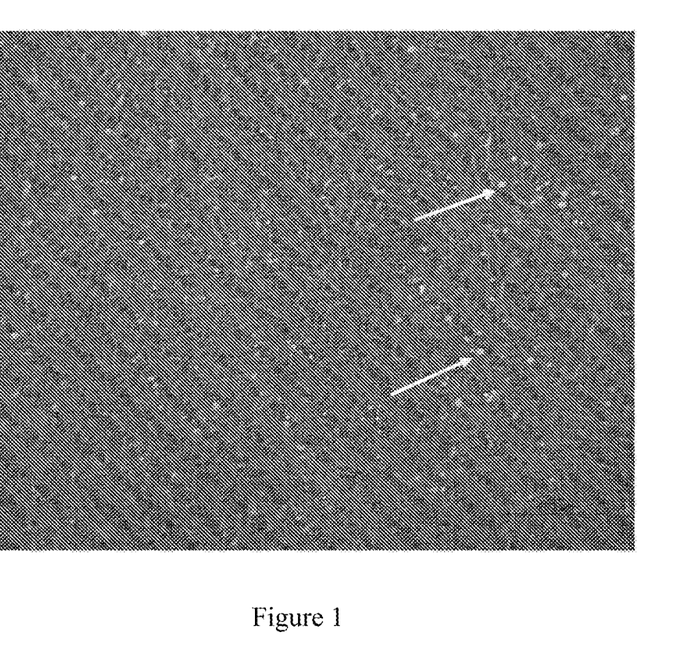
FIG. 1 shows an image of liver pathological changes, wherein the arrow indicates hepatocyte steatosis.
Figure 2:
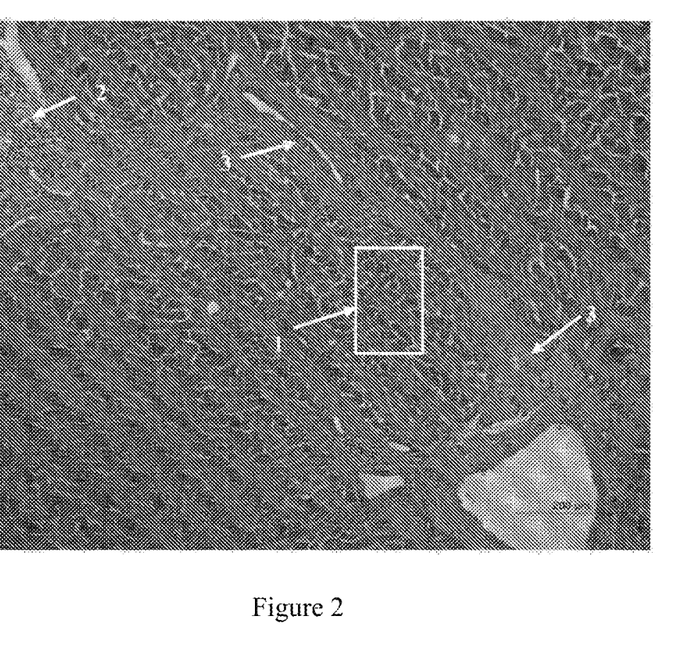
FIG. 2 shows an image of liver pathological changes, wherein arrow 1 indicates pseudolobuli, arrow 2 indicates a small amount of lymphocyte infiltration, and arrow 3 indicates liver fibroplasias.
Figure 3:
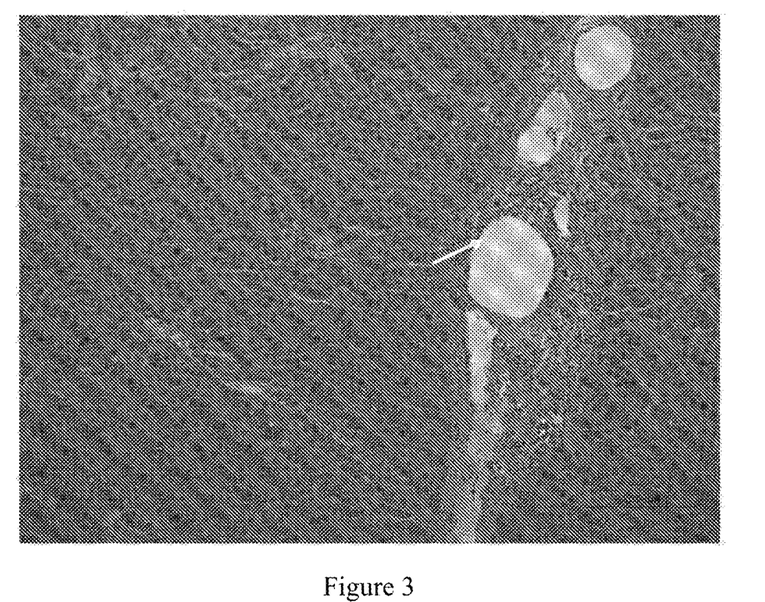
FIG. 3 shows an image of liver pathological changes, wherein the arrow indicates focal lymphocyte infiltration in the portal area.
Figure 4:
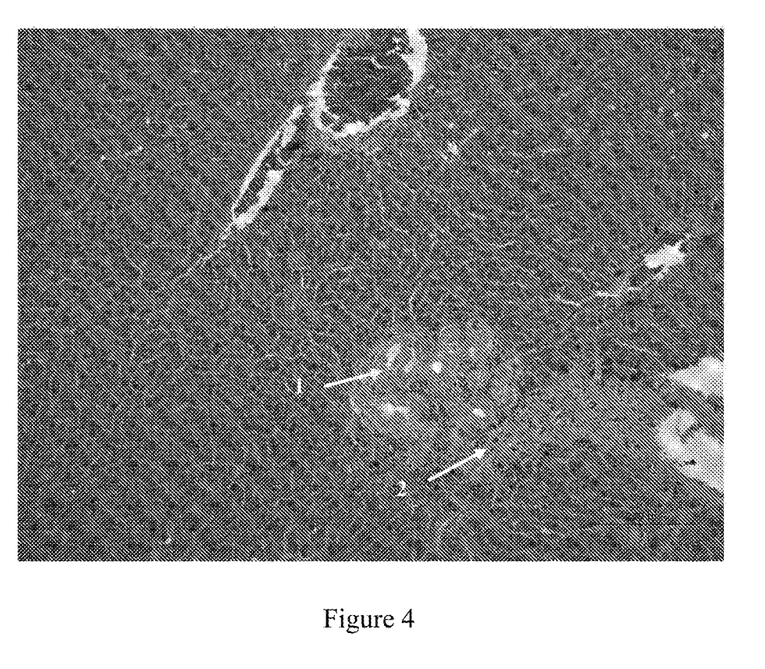
FIG. 4 shows an image of liver pathological changes, wherein arrow 1 indicates bile duct hyperplasia in the portal area, and arrow 2 indicates fibroplasias and inflammatory infiltration in the portal area.
Figure 5:
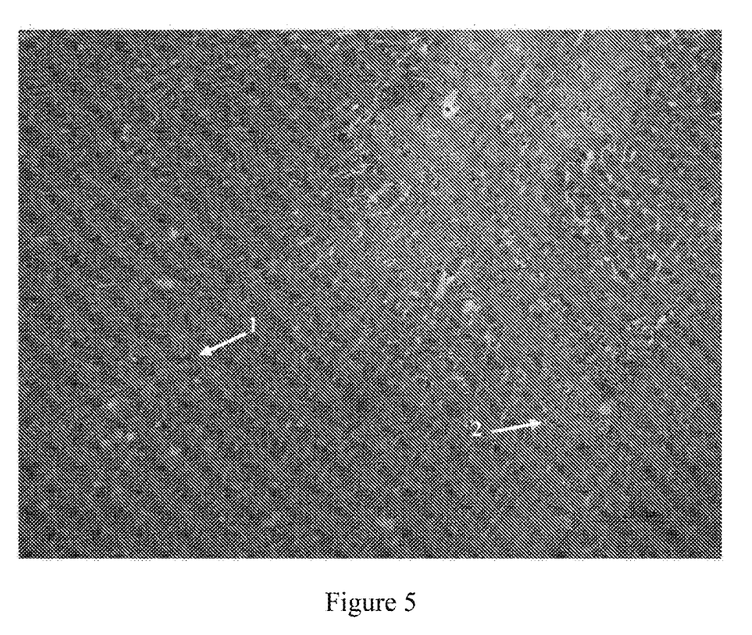
FIG. 5 shows an image of liver pathological changes, wherein arrow 1 indicates hemosiderosis and arrow 2 indicates focal lymphocyte infiltration.
Figure 6:
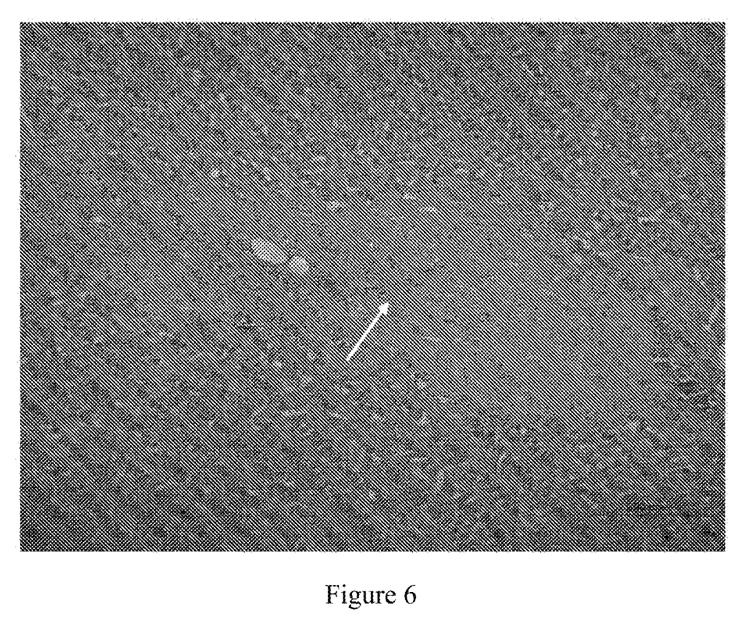
FIG. 6 shows an image of liver pathological changes, wherein the arrow indicates partial hepatocyte necrosis.

Main pathologic changes include: bile duct hyperplasia, liver fibrosis, pseudolobuli formation, hepatocyte steatosis, hemosiderosis, lymphocyte infiltration in the portal area, partial hepatocyte necrosis and the like (as shown in FIGS. 1-6). The scores of each pathologic change were accumulated. The experimental results were seen in Table 5.

TABLE 5

Scores of pathologic changes

| Group | Score Mean | | SD |
|---|---|---|---|
| Solvent control group (n = 9) | 1.71 | ± | 0.76 |
| Model group (n = 8) | 5.14 | ± | 1.96 |
| Low dosage group A (n = 8) | 3.71 | ± | 1.11 |
| High dosage group A (n = 8) | 4.00 | ± | 0.82 |
| Low dosage Group B (n = 8) | 4.43 | ± | 1.51 |

TABLE 5-continued

Scores of pathologic changes

| Group | Score Mean | | SD |
|---|---|---|---|
| High dosage group B (n = 8) | 3.29 | ± | 2.06 |
| Positive control group | 3.29 | ± | 1.38 |
| Treatment group C (n = 7) | 4.00 | ± | 1.00 |
| Treatment group D (n = 7) | 4.33 | ± | 1.53 |
| Treatment group E (n = 7) | 4.00 | ± | 0.00 |

It can be seen from the results that, the model group had an average score of the pathologic changes differing greatly from that of the blank group, indicating a more serious liver injury of the model group. The lower the score, the better the efficacy. The results demonstrate that, all the compositions A, B, C, D and E had a certain alleviating effect on the chemical liver injury. Although the high dosage group B had a lower score compared to other groups, the score had the largest standard deviation.

11. Conclusion

The traditional Chinese medicine composition in this experiment comprised Fructus Ligustri Lucidi, Herba Ecliptae, Radix Paeoniae Alba, clam extract and Rhizoma Curcumae Longae extract. Each medicine exhibited antioxidative and hepatoprotective effects. They constituted a reasonable composition to effectively alleviate liver injury, protect liver function and alleviate/postpone the occurrence of liver fibrosis. To sum up, the treatment group A and the treatment group B had a protective effect on liver injury caused by carbon tetrachloride in combination with hyperthermia traditional Chinese medicines and an inhibitory effect on liver fibrosis, and the treatment group A had a better effect. The partial formulations B, C and D had a certain alleviating effect on liver injury caused by carbon tetrachloride in combination with hyperthermia traditional Chinese medicines.

Only preferred embodiments of the present invention are described above. It should be noted that for those of ordinary skill in the art, several improvements and modifications may also be made without departing from the principle of the present invention, which is also to be regarded as within the protection scope of the present invention.

The invention claimed is:

1. A method for preparing a traditional Chinese medicine composition which consists of Fructus Ligustri Lucidi, Herba Ecliptae, Radix Paeoniae Alba, Rhizoma Curcumae Longae and clam as materials, the method comprising:
    1) extracting plant materials consisting of Fructus Ligustri Lucidi, Herba Ecliptae and Radix Paeoniae Alba with ethanol and concentrating the extract solution to obtain an alcohol extract of the three components;
    2) mixing the alcohol extract of Fructus Ligustri Lucidi, Herba Ecliptae and Radix Paeoniae Alba of step 1 with materials consisting of a Rhizoma Curcumae Longae extract and a clam extract to obtain the traditional Chinese medicine composition.

2. The method for preparing a traditional Chinese medicine composition according to claim 1, wherein the Rhizoma Curcumae Longae extract is an alcohol extract of Rhizoma Curcumae Longae and the clam extract is a water extract of clam.

3. The method for preparing a traditional Chinese medicine composition according to claim 1, wherein the parts by weight of the respective components are:

4-30 parts of Fructus Ligustri Lucidi, 2-15 parts of Herba Ecliptae, 2-15 parts of Radix Paeoniae Alba, 2-20 parts of the Rhizoma Curcumae Longae extract, and 2-10 parts of the clam extract.

4. The method for preparing a traditional Chinese medicine composition according to claim 3, wherein the parts by weight of the respective components are:

10-25 parts of Fructus Ligustri Lucidi, 5-15 parts of Herba Ecliptae, 3-12 parts of Radix Paeoniae Alba, 6-18 parts of the Rhizoma Curcumae Longae extract, and 4-8 parts of the clam extract.

5. The method for preparing a traditional Chinese medicine composition according to claim 4, wherein the parts by weight of the respective components are:

20 parts of Fructus Ligustri Lucidi, 15 parts of Herba Ecliptae, 8 parts of Radix Paeoniae Alba, 12 parts of the Rhizoma Curcumae Longae extract, and 8 parts of the clam extract.

6. The method for preparing a traditional Chinese medicine composition according to claim 2, wherein the Rhizoma Curcumae Longae extract is prepared by the following process:

grinding the Rhizoma Curcumae Longae, then extracting it with ethanol, concentrating the extract solution under reduced pressure into an extractum, adding ethanol to dissolve the extractum, filtering, concentrating the filtrate, and drying to obtain the Rhizoma Curcumae Longae extract.

7. The method for preparing a traditional Chinese medicine composition according to claim 2, wherein the clam extract is prepared by the following process:

washing the fresh clam, then boiling it with water, concentrating and filtering to obtain an extract solution of the clam, sterilizing, and then drying to obtain the clam extract.

* * * * *

UNITED STATES PATENT AND TRADEMARK OFFICE
CERTIFICATE OF CORRECTION

| | |
|---|---|
| PATENT NO. | : 10,799,549 B2 |
| APPLICATION NO. | : 16/412638 |
| DATED | : October 13, 2020 |
| INVENTOR(S) | : Yong Zhou et al. |

Page 1 of 1

It is certified that error appears in the above-identified patent and that said Letters Patent is hereby corrected as shown below:

On the Title Page

Item (71) Applicant, delete the entirety of the item and replace with --INFINITUS (CHINA) COMPANY LTD., Jiang Men City (CN)-- therefor.

Item (72) Inventors, delete the entirety of the items and replace with --Yong Zhou, Jiang Men City (CN); Hailong LI, Jiang Men City (CN); Xiaolei Guo, Jiang Men City (CN); Chung Wah Ma, Jiang Men City (CN)-- therefor.

Item (73) Assignee, delete the entirety of the item and replace with --INFINITUS (CHINA) COMPANY LTD., Jiang Men City, (CN)-- therefor.

Signed and Sealed this
Twelfth Day of January, 2021

Andrei Iancu
*Director of the United States Patent and Trademark Office*